(12) United States Patent
Ishimaru

(10) Patent No.: US 6,764,503 B1
(45) Date of Patent: Jul. 20, 2004

(54) STENT (OR STENT GRAFT) LOCATING DEVICE

(75) Inventor: Shin Ishimaru, 1-23-23, Jingumae, Shibuya-ku, Tokyo 150-0001 (JP)

(73) Assignee: Shin Ishimaru, Tokyo (JP)

(*) Notice: Subject to any disclaimer, the term of this patent is extended or adjusted under 35 U.S.C. 154(b) by 0 days.

(21) Appl. No.: 09/719,949

(22) PCT Filed: Feb. 24, 1999

(86) PCT No.: PCT/JP99/00824
§ 371 (c)(1),
(2), (4) Date: Dec. 18, 2000

(87) PCT Pub. No.: WO00/02615
PCT Pub. Date: Jan. 20, 2000

(30) Foreign Application Priority Data

Jul. 10, 1998 (JP) ............................................ 10-195558

(51) Int. Cl.[7] .................................................. A61F 2/06
(52) U.S. Cl. ........................ 623/1.11; 606/108; 606/191
(58) Field of Search ........................ 623/1.11; 606/191, 606/108, 198, 113, 200, 127, 206

(56) References Cited

U.S. PATENT DOCUMENTS

| | | | |
|---|---|---|---|
| 5,035,706 A | * 7/1991 | Gianturco et al. | 606/198 |
| 5,333,645 A | 8/1994 | Galazin | |
| 5,496,330 A | * 3/1996 | Bates et al. | 606/113 |
| 5,653,684 A | 8/1997 | Laptewecz et al. | 606/108 |
| 5,662,713 A | 9/1997 | Anderson et al. | |
| 5,665,115 A | 9/1997 | Cragg | |
| 5,683,451 A | * 11/1997 | Lenker et al. | 623/1.11 |
| 5,800,456 A | 9/1998 | Maeda et al. | |
| 5,824,058 A | * 10/1998 | Ravenscroft et al. | 623/1.11 |
| 5,843,167 A | 12/1998 | Dwyer et al. | |
| 5,902,334 A | 5/1999 | Dwyer et al. | |
| 5,961,546 A | 10/1999 | Robinson et al. | |
| 5,968,057 A | * 10/1999 | Taheri | 606/200 |
| 6,203,552 B1 | * 3/2001 | Bagley et al. | 606/127 |

FOREIGN PATENT DOCUMENTS

| | | |
|---|---|---|
| BE | WO 97/17021 A1 * | 5/1997 |
| JP | 2-172456 | 7/1990 |
| JP | 5-212121 | 8/1993 |
| JP | 6-98939 | 12/1994 |
| JP | 7-24072 | 1/1995 |
| JP | 7-500272 | 1/1995 |
| JP | 7-47134 | 2/1995 |
| JP | 7-504595 | 5/1995 |
| JP | 8-502428 | 3/1996 |
| JP | 8-511487 | 12/1996 |
| WO | WO 92/18195 | 10/1992 |
| WO | WO 94/00178 | 1/1994 |
| WO | WO 98/56449 | 12/1998 |

OTHER PUBLICATIONS

U.S. patent application Ser. No. 60/078,920.*
Copy of Examiner's first report on Australian Patent Application No. 25491/99.

* cited by examiner

Primary Examiner—Brian E. Pellegrino
(74) Attorney, Agent, or Firm—Butzel Long

(57) ABSTRACT

A stent locating device that includes leading wires, a pushing rod for holding the leading wires, and a sheath for loading the pushing rod. The pushing rod includes inner and outer tubes. The inner tube is used as a guiding wire channel. An annular portion between the inner and outer tubes is used as a leading wire channel. The pushing rod may be a single tube having a hollow portion that is used as a guiding wire channel and a plurality of leading wire channels arranged in the body thereof at regular intervals circumferentially. The pushing rod may have a plurality of leading wires, crossing leading wires, or a combination of leading wires and auxiliary leading wires which are distributed at regular intervals circumferentially and are derived from the tip of a leading wire channel(s).

16 Claims, 8 Drawing Sheets

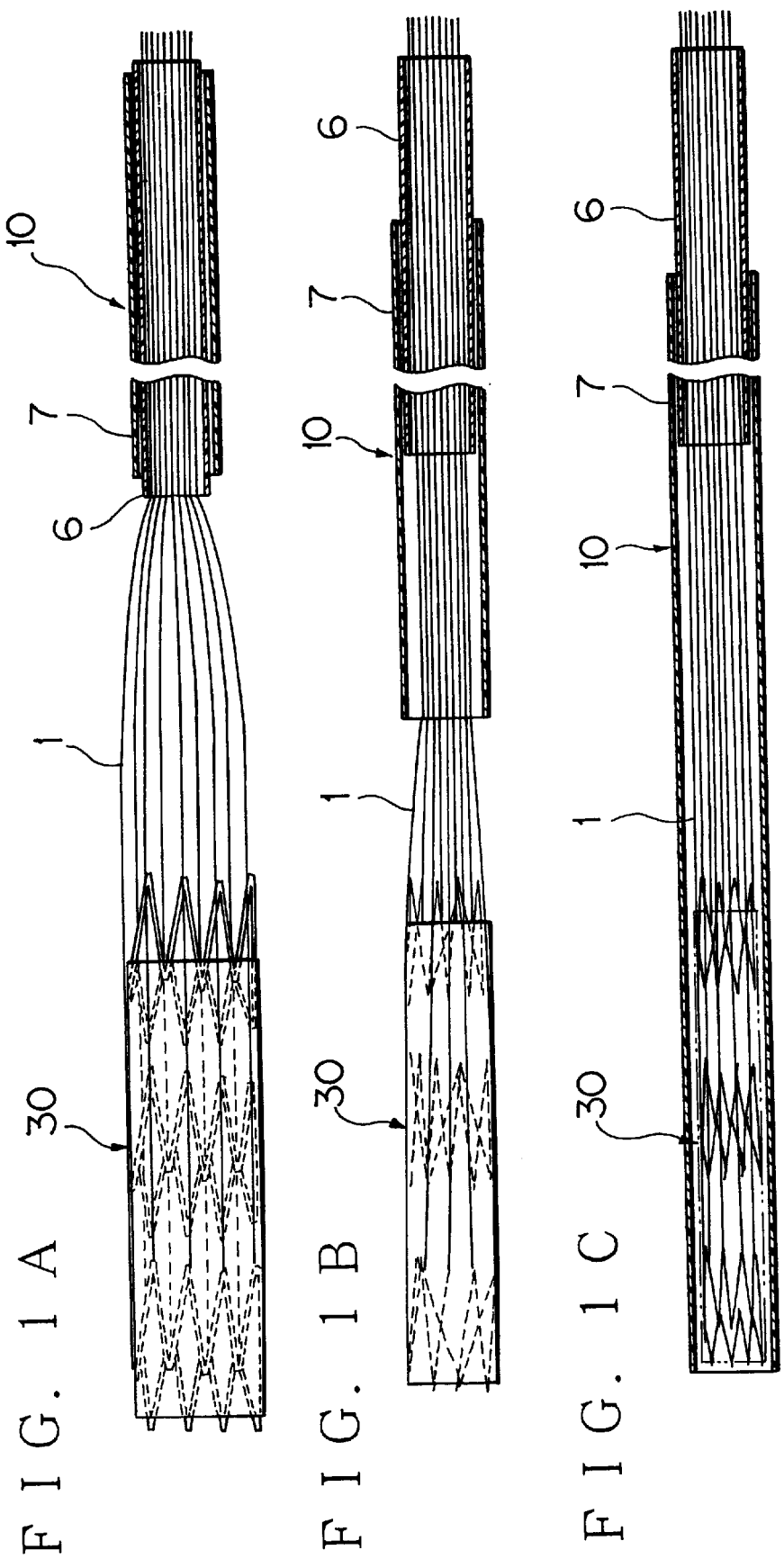

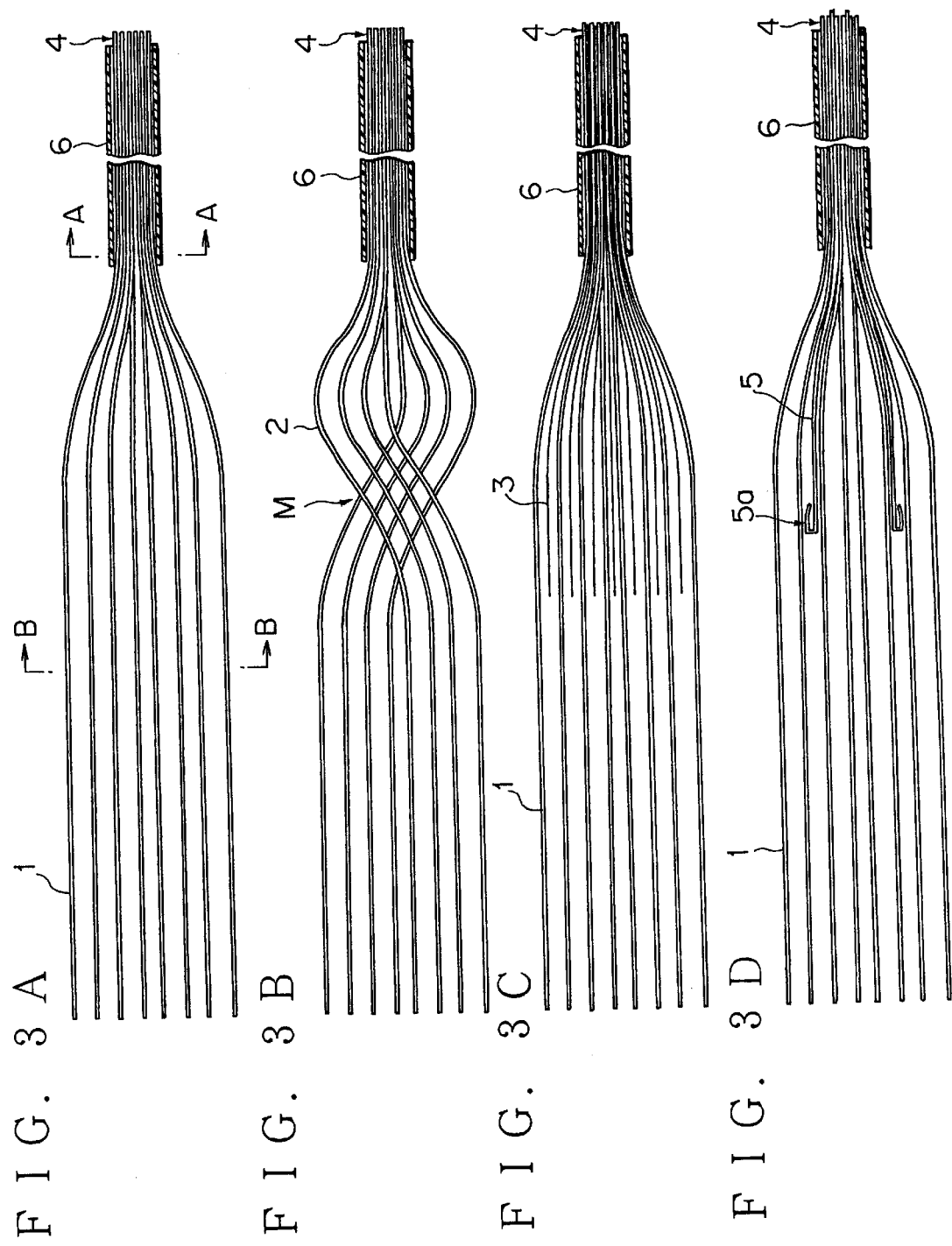

STENT (OR STENT GRAFT) LOCATING DEVICE

TECHNICAL FIELD

This invention relates to a device for safely locating a stent or stent graft at a diseased site in order to treat a stenotic and expansive disease such as an aneurysm of an artery and other disease conditions.

BACKGROUND ART

An aneurysm which grows due to hardening or inflammation of an artery, when left untreated expands gradually and fatally ruptures creating a disease condition that has no prognosis. Medicine has little effect on this type of disease condition. Therefore, in order to cure an aneurysm, a surgical operation using an artificial blood vessel, e.g. an operation involving removal of cancer tissue and of replacement by the artificial blood vessel has traditionally been performed. However, this type of disease condition is often experienced by old which increases the likelihood of multiple organ failure such as disorders of the brain, heart the kidneys, etc. In addition, the surgical operation is often excessively invasion. Thus, a surgical operation for this disease condition that is limited to safe technique which can avoid the danger of these difficulties is desired. Accordingly, much attention has been paid to the treatment of blood vessels using catheters which is less invasion.

A stent is an artificial tubular structure that is inserted into an internal tubular organ such as a blood vessel for the purpose of supporting it. When an internal tubular organ such as a blood vessel, gallbladder, esophagus, intestines, urethra, etc. suffers stenosis or deformation, stent is inserted into the internal tubular organ to support it so that the stenosis and deformation are prevented. A stent which has been widely applied clinically in order to treat an arterial stenotic disease is a cylinder formed of a wire mesh or spring made of stainless steel or a shape memory alloy (NiTi). The cylinder is formed to be shrinkable or expandable repeatedly in a radial direction. A stent graft is a polyester or Teflon artificial blood vessel in which a stent cylinder formed of mesh or a spring made of stainless or nickel titanium is sewed therein. Stent grafts have effectively been used to treat aneurysms. Such stents and stent grafts are disclosed in JP-A-7-24072, JP-A-7-47134, JP-A-7-500272 (PCT), JP-A-8-299456 (PCT), JP-A-8-502428 (PCT) and JP-A-8-511487 (PCT).

Stents and stent grafts are located in diseased portions of blood vessels through catheters. Specifically, the stent or stent graft is compressed to have a diameter smaller than the inner diameter of a fine catheter and is housed in the catheter. The stent or stent graft is inserted from an incised part of a peripheral artery such as a femoral artery into the diseased portion of the blood vessel. The stent or stent graft is extruded from the catheter and expanded to a prescribed diameter in a radial direction. The stent or stent graft is further located in the diseased portion of the blood vessel, thereby expanding an artery stenotic disease and closing the aneurysm while reconstructing a blood flow. The treatment using the stent or stent graft is acceptably invasive. Therefore, it can reduce the burden imposed on a patient, and can be also applied to aneurysm diseases. Thus, this treatment is effective for patients suffering from arterial stenotic diseases and expansive diseases.

However, conventional stents and stent grafts cannot be contracted again after they have been discharged from a catheter to expand and located in a blood vessel. Therefore, when a disorder of the blood stream and internal organ happen because of erroneous positioning of the stent or stent grafts, they cannot be moved or recovered.

Further, in order to ensure closure of an aneurysm conventional stent grafts must be located over a wider range including not only the aneurysm but also the normal artery on the central and peripheral sides of the aneurysm so that the contact between the stent graft and the internal face of the artery is assured. However, in this case, a problem is created when the stent graft also closes the main artery which branches from the vicinity of the aneurysm to generate organ disorder (hereinafter referred to as "position abnormality"). For example, in the case of an abdominal aortic aneurysm, when the artery such as a renal artery, inferior mesenteric artery, internal iliac artery, etc. is closed, there can be renal failure or colon ischemia. Likewise, in the case of a thoracic aortic aneurysm, when an intercostal artery is closed, there can be spinal cord ischemia, leading to serious complication of paralysis of a lower half of a patient's body.

The inventor of the present invention supposed as follows. It is assumed that a stent or stent graft which can recovered from the body can be located temporarily at a diseased portion of a blood vessel before the conventional stent or stent graft is located at the diseased part. In this case, if a dangerous portion where a blood flow disorder may occur when the conventional stent or stent graft is located in the blood vessel and a safe portion where no blood flow disorder exits are taken beforehand as video information, the conventional stent can be located at the safe point of the blood vessel. On the basis of this idea, the inventor of the present invention proposed a temporarily locating type stent or stent graft which can be recovered from the body after it is temporarily located (JP application No 9-151372).

Hereinafter, in the specification, a stent or stent graft which can be located temporarily at a diseased portion of a blood vessel is referred to as a "temporarily locating type stent or stent graft". On the other hand, the conventional stent or stent graft, which is permanently located at the diseased portion should be referred to as "permanently locating type stent or stent graft, but will be referred to as simply "stent or stent graft" as they are traditionally called.

In FIG. 12, reference numeral 111 denotes a temporarily locating type stent proposed by the inventor of the present invention. The temporarily locating type stent 111 is composed of a stent body 112 at the front and mast lines 118 at the rear. The stent body 112 has three elastic rings 114 each formed in a ring shape by a metallic wire bent in a zigzag manner. Each elastic ring 114 is made of a material such as stainless steel, titanium, shape memory alloy, etc. Around the elastic ring 114, eight coupling wires 115 are arranged at regular intervals in a circumferential direction of the ring. These coupling wires 115 are welded or soldered on the elastic rings 114 at their points of intersection of them to form an elastic cylindrical body 114. The elastic cylindrical body 113 is aligned with parallel portions 116 of the coupling wires 115. The mast lines 113 whose tips 119 are connected to the parallel portions 116 in the stent body 112 extend rearward as bundle. The coupling wires 115 and mast wires 11S are made of continuous shape memory alloy. The bundle of the mast wires 113 has a diameter which is slightly smaller than the inner diameter of a catheter 131. The mast wires 11S have a length sufficient to penetrate through the catheter 131 and to be operable outside the body when the stent body 112 is located at a prescribed position in a blood vessel. The stent body 112 and the mast wires 118 are sufficiently rigid to endure extrusion from the catheter 131 by manipulation from outside of the body and to be pulled into the catheter 131. The catheter 131 is equipped, at its outlet with an R-shape so that the stent body 112 can be contracted smoothly and received in the body.

The temporarily locating type stent or stent graft can be used to determine beforehand, as video information, the dangerous part where the blood flow disorder may happen in the diseased portion in e.g. the blood vessel, and a safe port where no blood flow disorder exists. This temporarily locating type stent permits the permanent locating type stent to be located on the safe point of the diseased portion. However, the temporarily locating type stent takes a long time for this use so that a patient is caused pain and burdened, and the procedure is costly.

The present invention intends to solve these problems.

More specifically, the present invention intends to provide a device for locating a stent or stent graft which can locate the stent or stent graft at a diseased portion safely, and reduce pain or burden for a patient and the cost required for the procedure.

DISCLOSURE OF INVENTION

In order to attain the above object, the present invention provides a stent or stent graft locating device comprising a number of leading wires, a pushing rod for holding the number of leading wires in its circumferential direction and a sheath for loading the pushing rod therein.

The invention further provides a stent or stent graft locating device in which a pushing rod is composed of an inner tube and an outer tube, a hollow portion of the inner tube is used as a guiding wire channel and another sectional ring-shaped hollow portion between the inner tube and the outer tube is used as a leading wire channel.

The invention further provides a stent or stent graft locating device in which a pushing rod is constructed of a single tube, a hollow portion of the tube is used as a guiding wire channel and a plurality of leading wire channels are arranged in a body of the tube at approximate regular intervals in its circumferential direction.

The invention also provides a stent or stent graft locating device in which a pushing rod has a plurality of leading wires which are derived from the tip of a leading wire channel and scattered at approximate regular intervals in the circumferential direction.

The invention further provides a stent or stent graft locating device in which a pushing rod has a plurality of leading wires which are derived from the tip of a leading wire channel and scattered at approximate regular intervals in the circumferential direction, and the plurality of leading wires cross in the vicinity of the tip of said pushing rod so as to form a coarse mesh.

The invention also provides a stent or stent graft locating device in which a pushing rod has a plurality of auxiliary leading wires which are finer and shorter than the leading wires are derived, among the number of leading wires, from the tip of said leading wire channel.

The invention further provides a stent or stent graft locating device in which a pushing rod has plural lead-in wires which are derived from the tip of the leading wire channel and engaged with the knees at the terminal of the stent at approximate regular intervals by detachable engaging means.

The invention also provides a stent or stent graft locating device having an engaging means which is a hook formed by bending the tip of each of the lead-in wires.

The invention moreover provides a stent or stent graft locating device having an engaging means that is a ring screwed into the tip of each of the lead-in wires.

The invention further provides a stent or stent graft locating device having leading wires that are metallic wires of stainless steel, titanium nickel or nickel.

The invention further provides a stent or stent graft locating device having auxiliary leading wires that are metallic wires or stainless steel, titanium nickel or nickel.

The invention moreover provides a stent or stent graft locating device having lead-in wires that are metallic wires of stainless steel, titanium nickel or nickel.

The invention also provides a stent or stent graft locating device in which the stent or stent graft is encircled by a number of leading wires and housed in a sheath.

The invention also provides a stent or stent graft locating device in which the tip of each of a number of leading wires is seamed with an elastic ring-shaped portion of a stent or stent graft by a joining thread.

BRIEF DESCRIPTION OF DRAWINGS

FIGS. 1A–1C are partially broken side views of a stent graft locating device according to an embodiment of the present invention. FIG. 1A shows a state in which a stent graft fixedly encircled by a number of leading wires has been extruded from a sheath. FIG. 1B shows a state in which the stent graft fixedly encircled by a number of leading wires is to be pulled into the sheath. FIG. 1C shows a state in which the stent graft fixedly encircled by a number of leading wires has been housed within the sheath.

FIG. 2A shows a state in which the leading wires encircling the stent graft are being pulled out. FIG. 2B shows a state in which all the leading wires have been pulled out to locate the stent graft permanently at a diseased portion. FIG. 2C shows a state in which the leading wires encircling the stent graft and lead-in wires are being pulled out. FIG. 2D shows a state in which all the leading wires and the lead-in wires have been pulled out to locate the stent graft permanently at a diseased portion.

FIGS. 3A–3D are conceptual views of a pushing rod for holding a number of leading wires arranged in the circumferential direction. FIG. 3A shows the pushing rod with a number of parallel leading wire 5 arranged in the circumferential direction. FIG. 3B shows the pushing rod with a number of crossing leading wires arranged in the circumferential direction. FIG. 3C shows the pushing rod with a number of parallel leading wires and auxiliary leading wires arranged in a circumferential direction. FIG. 3D shows the pushing rod with a number of leading wires and lead-in wires arranged in the circumferential direction.

FIG. 10A shows a hook and FIG. 10B shows a ring.

BEST MODE OF CARRYING OUT THE INVENTION

Figure 2A:
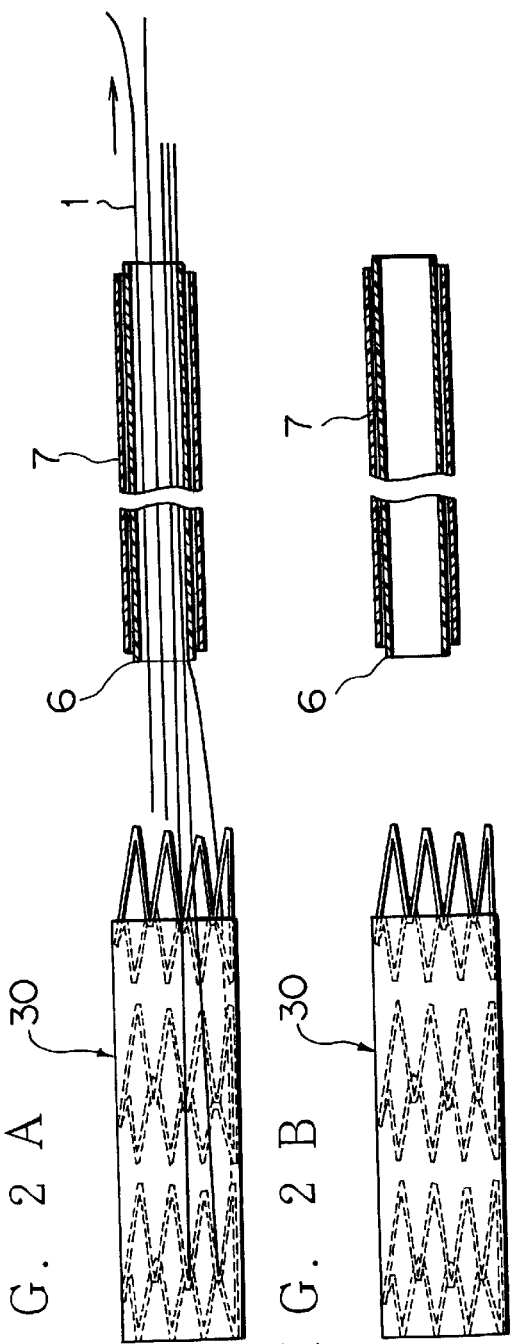
FIGS. 2A–2D are partially broken side views of a stent graft extruded from a sheath.

Referring to the drawings, an explanation will be given of various embodiments of the invention. In FIG. 1, reference numeral 10 denotes a stent graft locating device. The stent graft locating device 10 includes a number of leading wires 1, a pushing rod 6 for holding the number of leading wires 1 arranged in the circumferential direction and a sheath 7 in which the pushing rod 6 is loaded.

As seen from FIGS. 3A to 3D, the pushing rod 6 holds therein a number of leading wires 1 arranged in the circumferential direction as a bundle. The pushing rod 6 is structured in the following configurations with the leading wires 1 arranged in its outside: (1) The leading wires 1 guided from the tip of the leading wire channel (see 6D and 6c in FIGS. 4A and 4B) are arranged at approximate regular intervals in the circumferential direction (FIG. 3A); (2) The leading wires 1 guided from the tip of the leading wire channel are arranged at approximate regular intervals in the circumferential direction, and cross to form a coarse mesh (M) in the vicinity of the tip of the pushing rod 6 (FIG. 3B); (3) auxiliary leading wires which are finer and shorter than the leading wires are derived, among the number of leading wires, from the tip of the leading wire channel (FIG. 3C); and plural lead-in wires 5 are derived from the tip of the leading wire channel and engaged with the knees (11a in FIG. 9) at the terminal of the stent at approximate regular intervals by detachable engaging means 5a (FIG. 3D).

Figures 4A, 4B:
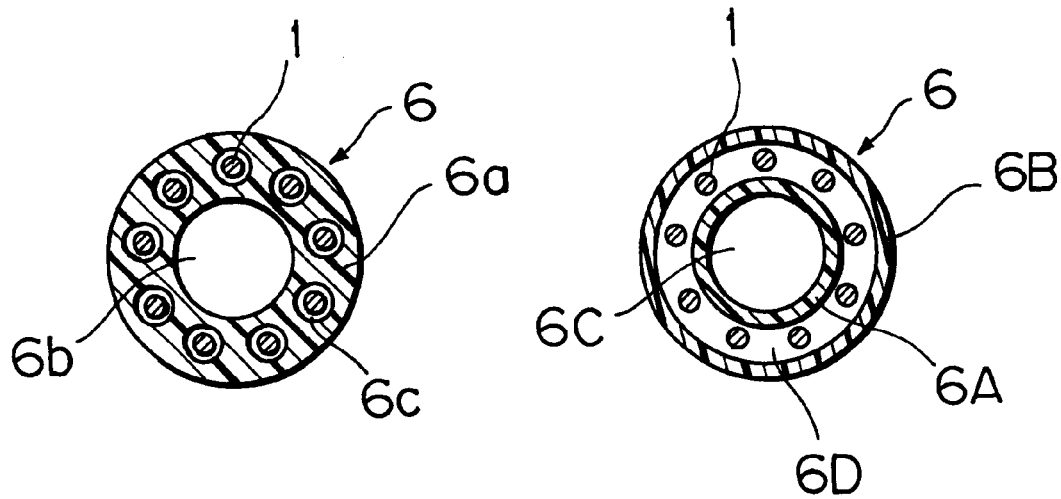
FIG. 4A is a sectional view taken in line A—A in FIG. A3 of the pushing rod having, as leading wire channels, a sectional ring-shaped hollow portion between an inner tube portion and an outer tube portion.
FIG. 4B is a sectional view of the pushing rod with a number of leading wire channels formed at approximate regular intervals in the circumferential direction within a tube body.
Figure 5:
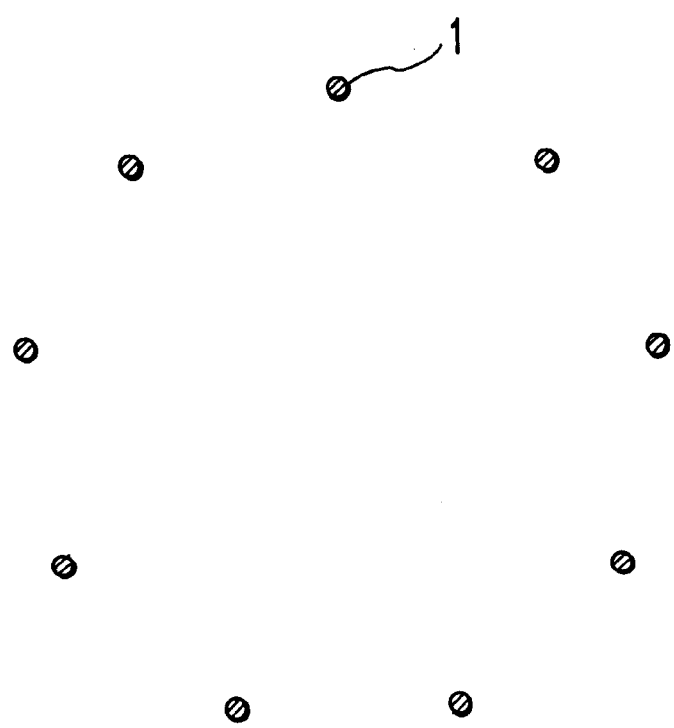
FIG. 5 is a sectional view taken in line B—B in FIG. 3A.

As seen from FIG. 4A, the pushing rod 6 may be composed of an inner tube 6A and an outer tube 6B so that the hollow portion of the inner tube 6A is used as a guiding wire channel 6C and the sectional ring-shaped hollow portion between the inner tube 6A and the outer tube 6B is used as a leading wire channel 6D. The guiding wire channels 6b and 6C are provided to guide the pushing rod 6 along a guiding wire (not shown). Further, as seen from FIG. 48, the pushing rod 6 is made from a flexible tube so that the hollow portion of the tube is used as a guiding wire channel 6b and a number of leading wire channels 6c are formed within the body 6a of the tube at approximate regular 10 intervals in the circumferential direction. The leading wires 1 are passed through the leading wire channels 6c, respectively, or through the leading wire channel 6D. These leading wires are arranged in the circumferential direction to form a bundle thereof (4 in FIGS. 3A–3D). The illustrated embodiment of a pushing rod which holds a number of leading wires arranged in the circumferential direction is exemplary, and may take any other structure as long as it accords to the object of the present invention.

The auxiliary leading wires 3 may be arranged among the leading wires 2 as shown in FIGS. 3B and 3D.

The leading wires 1, leading wires 2, auxiliary leading wires 3 and lead-in wires 5 may be made of stainless steel, nickel titanium, or nickel. These metallic wires are preferably used, and may be replaced by any other metallic wire as long as they are not contrary to the object of the present invention. The leading wires 1, leading wires 2, auxiliary leading wires 3 and lead-in wires 5 may be rigid plastic wires of resin such as (1) acrylic resin, (2) polyolefin (polyethylene, polypropylene, etc.), (3) polyester, (4) polyamide, etc., or enforced plastic composed of these resins and any of the above metals, glass fiber, carbon fiber, etc.

Figure 9:
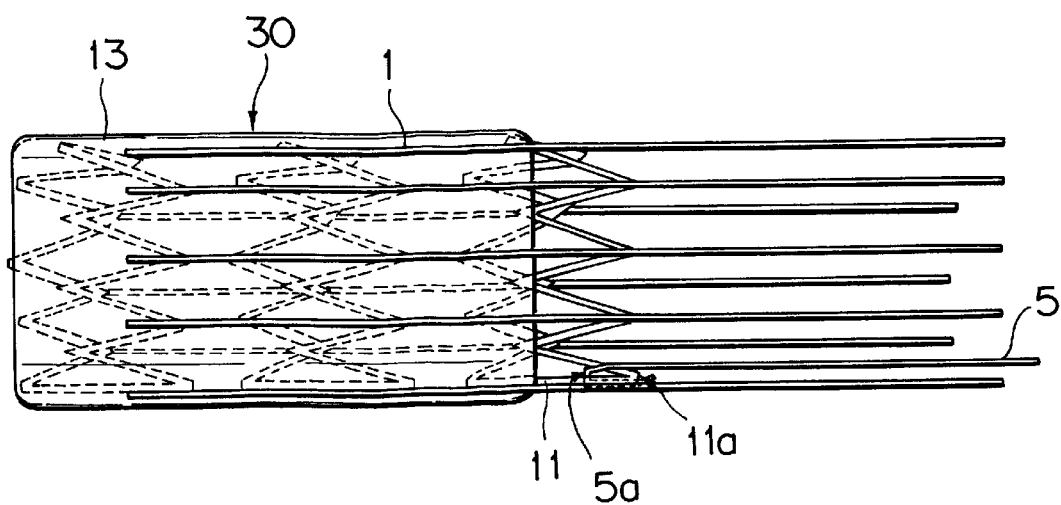
FIG. 9 is an enlarged view depicting a state in which lead-in wires are engaged with the stent graft held to be encircled by a number of leading wires and extruded from a sheath.

The leading wires 1, leading wires 2, auxiliary leading wires 3 and lead-in wires 5 have a diameter of e.g. 0.4–0.8 mm. Although a plurality of leading wires 1 are depicted in the figures, the number thereof only has to be enough to hold the stent graft encircled thereby. In FIG. 9, although nine leading wires 1 are illustrated, the number; thereof may be changed according to the size of the stent graft. The plurality of leading wires 1 are arranged at intervals in the circumferential direction within the pushing rod 6 to form a bundle. Therefore, even when they are manipulated from the outside of the body by pulling the pushing rod 6 in and out through the sheath 7 to the outside of the body, it will not be bent. The leading wires 1 sufficient lengths to hold the stent graft 30 in the vicinity of their tips and enable the stent graft to reach the diseased portion of e.g. a blood vessel.

Figure 11:
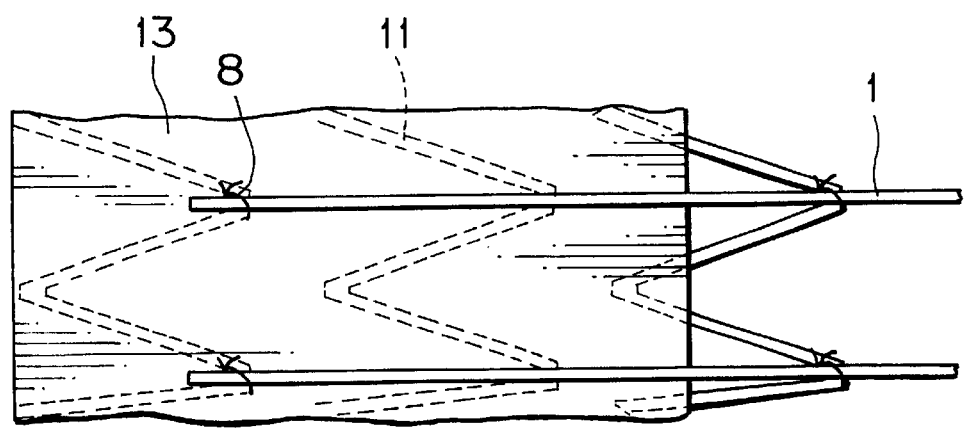
FIG. 11 is a partially enlarged view depicting the stent graft shown in FIG. 8.
Figure 12:
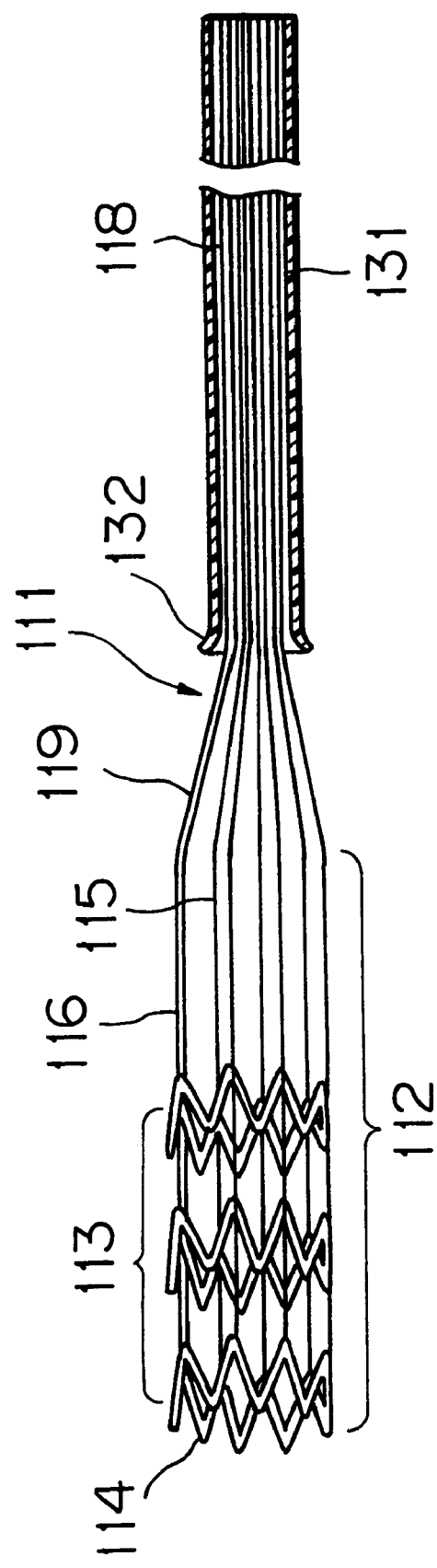
FIG. 12 is a perspective view of a temporarily locating type stent in which the stent body has been extruded from a catheter and expanded.

As shown in FIG. 1C, the stent graft 30 being fixedly encircled by the plurality of leading wires may be housed within the sheath 7. In this case, as shown in FIG. 11, the tips of the plurality of leading wires may be sewn with the stent graft 30 at its elastic rings 11 by joining threads 3, respectively. In this way, the stent graft 30 can be held securely by the number of leading wires 1. These leading wires 1, which have high sliding smoothness, can be easily pulled out.

As seen from FIG. 3A, when the pushing rod 6 has a number of leading wires 1 derived from its tip and arranged at approximate intervals in the circumferential direction, the stent or stent graft (not shown) to be permanently located at the diseased part of the blood vessel can be expanded or contracted freely in such a way that it is squeezed out of or retracted in the tip of the sheath (7 in FIGS. 1A–1C). Therefore, if there is a positioning error, the stent or stent graft housed in the sheath again can be moved to and located at a safe region in the diseased portion. Also, if there is an impossibility of expansion, the stent or stent graft housed in the sheath again can be discharged again. As seen from FIG. 38, where the pushing rod 6 has the leading wires 2 derived from its tip and arranged at approximate regular intervals in the circumferential direction, and crossing to form a coarse mesh (M) in the vicinity of the tip of the pushing rod 6, the stent graft can be wrapped in the crossing portion of the leading wires 2 and restricted strongly therein. Therefore, even when the leading wires 2 are slender, the stent graft can be housed smoothly within the sheath. As seen from FIG. 3C, where the pushing rod 6 has the auxiliary leading wires 3 which are finer and shorter than the leading wires 1 among the number of leading wires, when the stent graft is pulled in the sheath, it is possible to prevent the stent from being crinkled to be hooked by the tip of the sheath. Further, as seen from FIG. 3D, where the pushing rod 6 has a plurality of lead-in wires 5 derived from the tip of the leading wire channel (6D and 6c in FIGS. 4A and 4B) and engaged with the knees (11a in the elastic ring 11 in FIG. 9) at the terminal of the stent at approximate regular intervals by detachable engaging means (hook 5a), the stent or stent graft can be led into the sheath 7 by the leading wires 1 fixed on the outer surface of the stent and the detachable lead-in wires 5 attached to the terminal of the stent (knees 11a in the elastic ring 11 in FIG. 9). Also when the engaging means has the form of a ring 5b (FIG. 10B), the same operation can be obtained.

Now referring to the drawings, an explanation will be given of the operation of the stent graft according to the invention.

Figure 8:
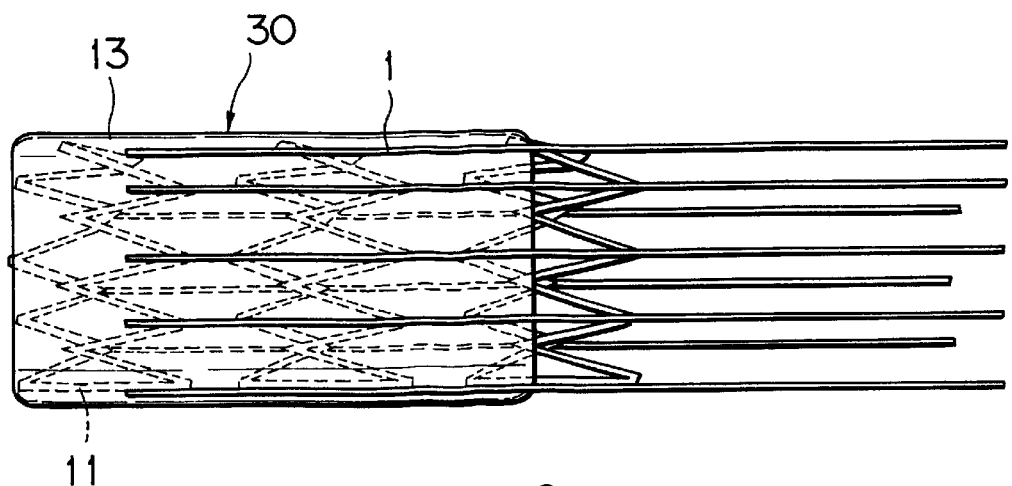
FIG. 8 is an enlarged view depicting a state in which a stent graft fixedly encircled by a number of leading wires has been extruded from a sheath.

As seen from FIG. 1A and FIG. 8, the stent graft 30 is encircled in the circumferential direction by the number of leading wires 1. As shown in FIG. 11, the leading wires 1 are sewn with the stent graft 30 at its elastic rings 11 by junction threads 8. Thereafter, as seen from FIG. 1B, the pushing rod 6 that extends through the sheath to outside of the body is pulled gradually so that the number of leading wires 1 is retracted into the sheath 7. As shown in FIG. 1C, the stent graft 30 is folded and contracted to have a smaller diameter than the inner diameter of the sheath 7. In this way, the stent graft 30 is housed in the sheath 7. The stent graft 30 can be housed previously or immediately before use in the sheath 7.

Figure 10:
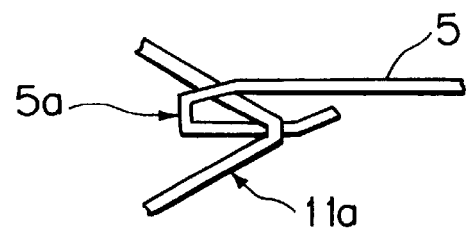
FIGS. 10A–10B are enlarged views depicting the means for engaging the lead-in wires with the stent.
Figure 10:
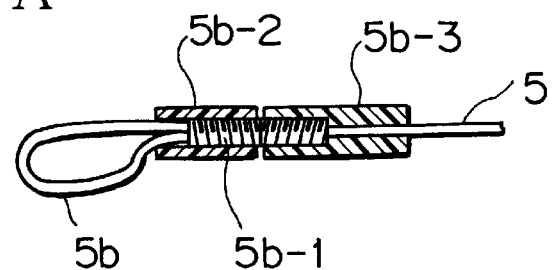

In this case, where the pushing rod 6 has the lead-in wires 5, as shown in FIGS. 10A and 10B, the engaging portion of the lead-in wire 5, i.e. hook 5a or ring 5b is engaged with the knee 11a of the elastic ring 11. In the case of the ring 5b, its one end is fixed to the inner wall of a ring-shaped fixing member 5b-1 by welding or soldering. After the ring 5b is engaged with the knee 11a of the elastic ring 11, its other end is inserted in the ring-shaped fixing member 5b-1 and a tightening member 5b-2 is screwed on the screw cuts on the front surface of the ring-shaped fixing member 5b-1. The lead-in wire 5 is fixed into the inner wall of a ring-shaped lead-in wire fixing member 5b-3 by welding or soldering. The lead-in wire 5 is wound so that the lead-in wire fixing member 5b-3 is screwed on the rear surface of the ring-shaped fixing member 5b-1. The screw cuts on the front surface and rear surface of the ring-shaped fixing member 5b-1 are formed by combining a right-hand threads and a left-hand threads.

Figure 2B:
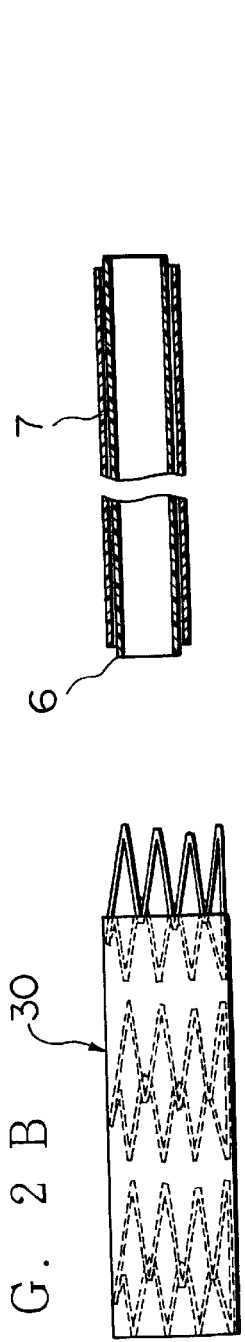

The stent graft 30 housed in the sheath 7 (FIG. 1C) is inserted into the body from an incised portion of a peripheral artery such as a femoral artery along the guiding wire to reach the diseased part of the blood vessel. Thereafter, the far end of the pushing rod 6 is pushed so that the stent graft is squeezed into the artery to expand and be located to close the aneurysm and reestablish the blood flow simultaneously (FIGS. 1A and 1B). In this case, when it is found from the video information that an unexpected accident such erroneous location and nonexpansion of the stent graft 30 has happened, the leading wires 1 are pulled so that the stent graft is housed in the sheath 7 again while it is converged (FIG. 1C). After the sheath 7 is positioned again, the stent graft 30 is located at the aneurysm in the same manner as described above. Thereafter, as shown in FIG. 2A, the leading wires 1 are pulled out of the body one by one through the pushing rod 6. Thus, as shown in FIG. 2B, the stent graft 30 is left at the diseased portion of the blood vessel and permanently located there. In this way, in accordance with the present invention, by finding a safe point from the video image which is out of the dangerous point where blood flow disorder happens when the stent graft 30 is located in the blood vessel 30, the stent graft 30 can be located safety in the aneurysm. The leading wires 1 are pulled out of the body one by one through the pushing rod so that as shown in FIG. 2B, the stent graft 30 is left and permanently located at the diseased part in the blood vessel.

Figure 2C:
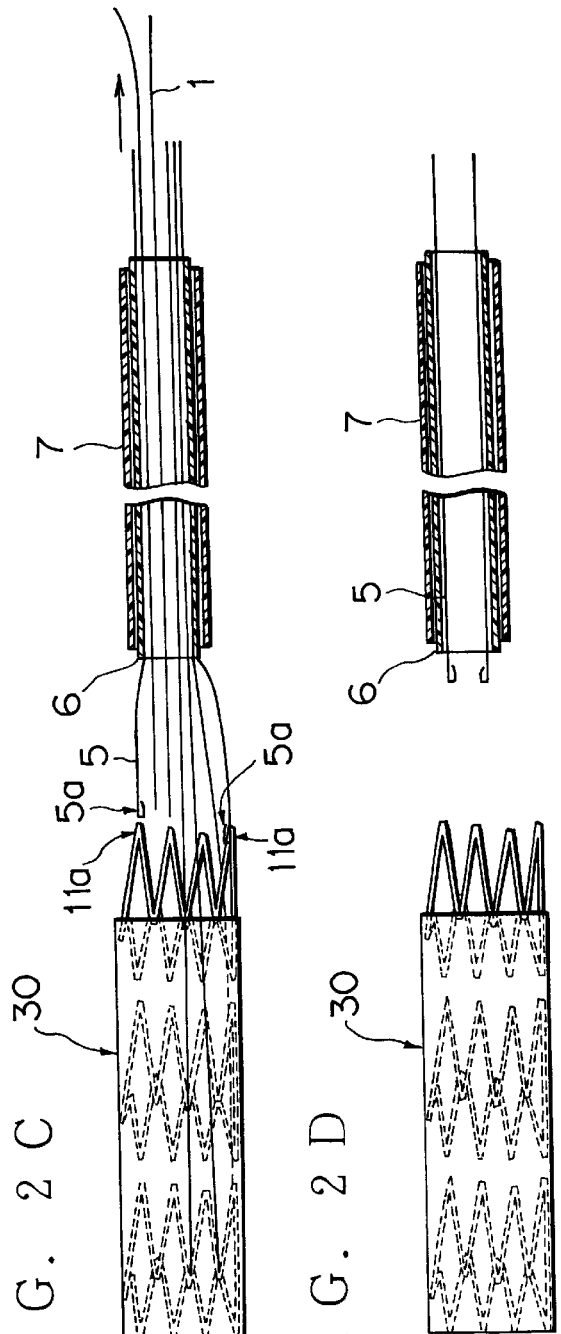
Figure 2D:
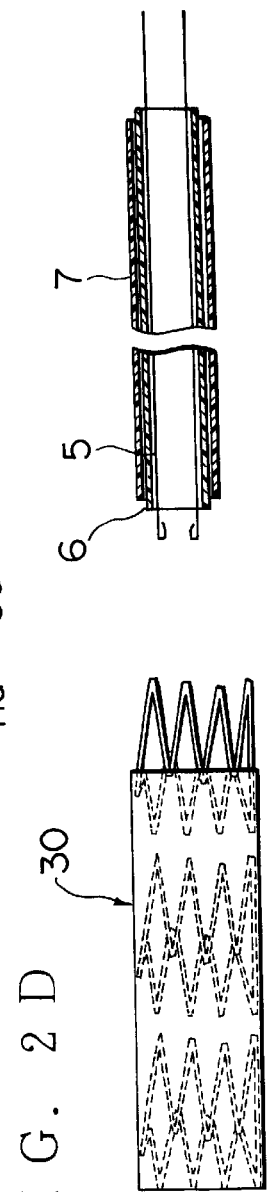

In this case, where there are auxiliary leading wires 3, like the leading wires 1, they are pulled out of the body one by one through the pushing rod 6. Further, where there are leading-in wires 5, as shown in FIG. 2C, the leading wires 1 are pulled out one by one through the pushing rod 6, and further the means, i.e. hook 5a, engaged with the terminal of the stent (knee 11a of the elastic ring 11) is taken off by pushing the lead-in wires 5 derived out of the body. Thereafter, the lead-in wires 5 are pulled out one by one through the pushing rod. FIG. 2D shows a state in which the lead-in wires 5 have been pulled into the pushing rod 6. In this case, the engaging means (hook 5a) remains held at the tip of the leading wire channel (not shown). Where the engaging means is a ring 5b, the lead-in wire 5 derived out of the body is wound so that the lead-in wire fixing member 5b-3 is taken off from the ring-shaped fixing member 5b-1 at the screwed portion. Thereafter, the lead-in wires 5 are pulled out of the body one by one through the pushing rod 6.

Thereafter, the pushing rod 6 held in the sheath 7 is taken out of the body 6 (FIG. 2B and FIG. 2D) is taken out of the body together with the sheath 7.

The leading wires, auxiliary leading wires, lead-in wires, pushing rod and sheath are washed and sterilized. They will be used again.

The stent graft 30 housed within the sheath 7 can be inserted into the body 30 as follows. Previously, a guiding wire (not shown) is inserted from the incised portion of the femoral artery which is a peripheral artery to reach the incised portion of the brachial artery through the diseased portion of the blood vessel. The one end of the guiding wire derived from the incised portion of the femoral artery is passed through the guiding wire channel 6b (6C) of the pushing rod. By guiding the stent graft 30 housed within the sheath 7 using the guiding wire, it can be inserted from the incised portion of the femoral artery to reach the diseased part of the blood vessel.

In this way, the stent graft 30 is permanently located at the diseased portion within the blood vessel so that expansion of the artery stenosis lesion and closing of the aneurysm are carried out while the blood flow is reestablished.

Figure 6:
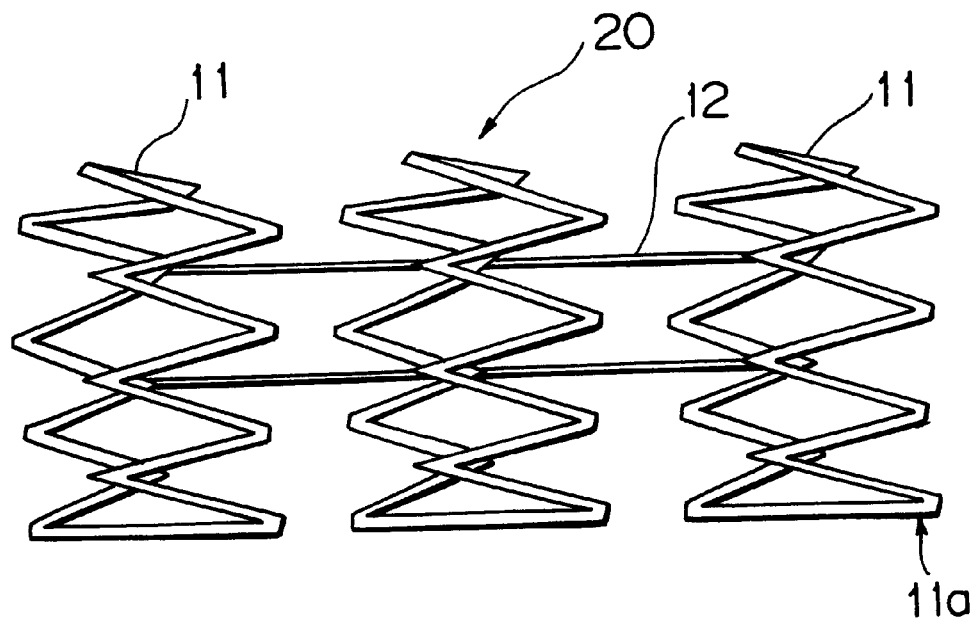
FIG. 6 is an enlarged side view of a stent according to the present invention.

The details of the stent 20 are shown in FIG. 6. The stent has an outer diameter of 20–40 mm when it is expanded and has a length of 30–100 mm. The stent 20 has a plurality (three in the drawing) of elastic rings 11 each formed in ring shape by a metallic wire bent in zigzag. The elastic rings are arranged at regular intervals in the axial direction of the stent. Around the elastic ring 11, coupling wires 12 are arranged at regular intervals in the circumferential direction. These coupling wires 12 are welded or soldered on the elastic rings 11 at their points of intersection of them. The elastic rings 11 and the coupling wires 12 are made of the metal having rigidity such as stainless steel, titanium, nickel titanium, etc. The metallic wire has a diameter of about 0.4–0.8 mm. The stent 20 may be constructed of a mesh of these metallic wires (not shown).

Figure 7:
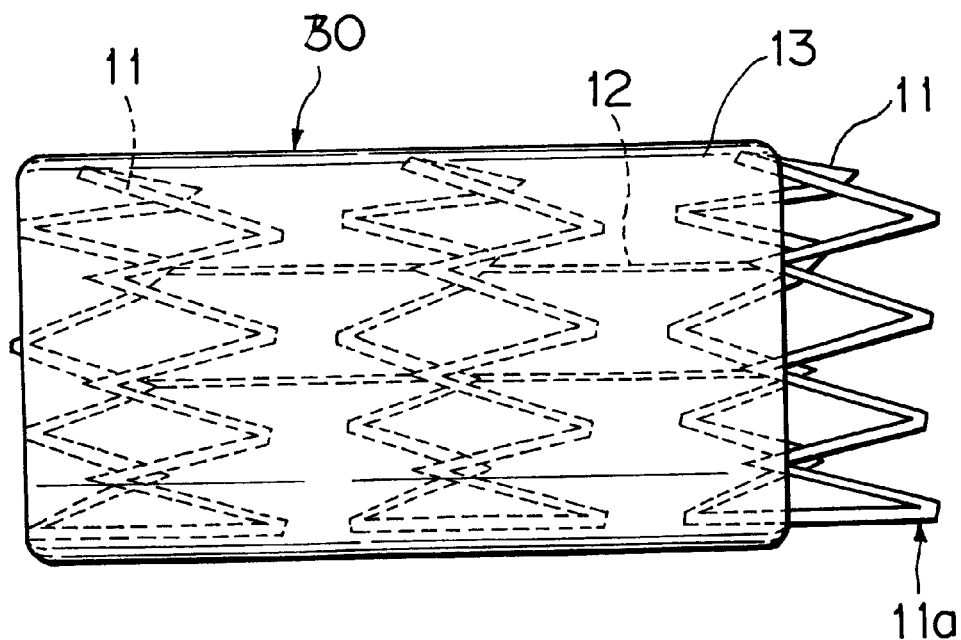
FIG. 7 is an enlarged side view of a stent graft according to the present invention.

The details of the stent graft are shown in FIG. 7. The stent graft 30 is structured so that the stent 20 described above is inserted in a graft 13 (artificial blood vessel) of polyester or Teflon (PTFE) and the graft 13 is sewn with the elastic rings 11 by threads of polypropylene (not shown).

The mode of carrying out the invention was explained mainly on the stent graft, the invention can be applied to the stent in a similar manner.

Embodiment

Referring to the drawings, an embodiment of the invention will be explained below.

As seen from FIG. 6, a stent 20 is composed of three elastic rings 11 each made of a metallic wire of a shape memory alloy (NiTi) and formed in a spring shape, which are coupled by means of coupling wires 12 each made of the metallic wire by welding or soldering. The stent 20 is sewn into a graft (artificial blood vessel) 13 of Teflon (PTFE) as shown in FIG. 7 to form a stent graft 30. On the other hand, the guiding wire (not shown) is previously inserted from the incised portion of a peripheral artery such as a femoral artery in a thoracic aortic aneurysm model to reach the incised portion of the brachial artery through the diseased part of the blood vessel. The guiding wire derived from the incised portion of the femoral artery is passed into the hollow portion of the stent graft 30 and into the guiding wire channel 6b (6C) (FIGS. 4A and 4B) of the pushing rod 6 in the stent graft locating device 10 as shown in FIG. 1A. The far end of the guiding wire is extended out of the sheath 7.

The stent graft 30 is fixedly encircled by nine leading wires 1. Two lead-in wires 5 are removably attached to the terminal of the stent (knees 11a of the elastic ring 11) at regular intervals by means of the hooks 5a. The pushing rod 6 is pulled so that the stent graft 30 encircled by the nine leading wires 1 and two lead-in wires 5 is folded to have a diameter smaller than the internal diameter (18–20 French (6 mm–6.667 mm)) of the sheath 7. In this case, the number of leading wires 1 and lead-in wires 5 are arranged in the circumferential direction. The far end of the bundle 4 of the leading wires 1 and lead-in wires 5 is extended out of the sheath 7 through the leading wire channel 6c of the pushing rod 6.

As shown in FIG. 1C, the stent graft 30 housed in the sheath 7 is inserted from the incised portion of the peripheral artery along the guiding wire to reach the diseased portion of the blood vessel. Thereafter, as shown in FIGS. 1B and 1C, the stent graft encircled by the number of leading wires is extruded from the tip of the sheath 7 by the pushing rod 6 so that it is discharged into the diseased portion of the blood vessel and temporarily located there, otherwise recovered into the sheath 7 by the lead-in wires 5 and temporarily housed therein. Thus, the safe point is found from the video image which is out of the dangerous point where blood flow disorder happens when the stent graft 30 is located in the blood vessel. Thereafter, as shown in FIG. 2C, with the stent graft 30 expanded at the safe point, the leading wires 1 and lead-in wires 5 are pulled out one by one so that as shown in FIG. 2D, the stent graft 30 is permanently left at the diseased part in the blood vessel. When liquid is circulated through the thoracic aortic aneurysm model, a good operation result was acquired.

Industrial Applicability

In accordance with the invention, the expansion, contraction, movement and recovery of the stent (or stent graft) to be located permanently can be controlled freely outside a human body. Therefore, by pulling out or in the stent or stent graft from the tip of the sheath at the diseased portion in the blood vessel, i.e. freely expanding or contracting it, it can be located accurately at a safe point.

In accordance with the invention, when it is found that the stent or stent graft to be used is not suited to medical treatment, it can be recovered. This improves safety of the treatment.

In accordance with the invention, since the blood vessel can be treated using the stent or stent graft which is right in an operation invasion, it is possible to reduce pain and burden for a patient in the treatment for the blood vessel and the cost of the treatment. Therefore, the treatment using the stent (or stent graft) can also be applied to the treatment of aneurysm that have been untreatable in a large number of patients.

The present invention can be applied to the stent or stent graft having various structures and sizes which are different according to manufactures and objects of use. The stent according to the invention can be recovered for its reuse, thus providing great economic effects.

In accordance with the present invention, the pushing rod has a large number of parallel leading wires which are derived from the tip of the pushing rod and arranged in the circumferential direction, and these leading wires cross to form a coarse mesh in the vicinity of the tip of the pushing rod. Because of this configuration, the entire stent graft can be encompassed by a small number of leading wires, and the stent graft can be smoothly recovered into the sheath.

In accordance with the present invention, since the pushing rod has auxiliary leading wires which are shorter than the leading wires 1 among the number of leading wires, when the stent graft is pulled in the sheath, it is possible to prevent the stent from being crinkled to be hooked by the tip of the sheath.

In accordance with the present invention, the stent or stent graft can be pulled into and housed in the sheath using the detachable lead-in wires 5 which are engaged with the knees of the elastic ring at the terminal of the stent or stent graft by the engaging means such as a hook or ring. Therefore, the discharge/expansion and the contraction/housing of the stent or stent graft can be repeated. Accordingly, the stent or stent graft can be located at a more preferred point swiftly.

What is claimed is:

1. A stent (or stent graft) locating device comprising a number of rigid leading wires, a pushing tube assembly for holding the number of rigid leading wires in its circumferential direction, said pushing tube assembly having a terminal end, the number of rigid leading wires being axially movable independent of one another within the pushing tube assembly, and a sheath for loading the tube assembly therein, said number of rigid leading wires each having a free terminal end configured to extend beyond the terminal end of the pushing tube assembly.

2. A stent (or stent graft) locating device according to claim 1, wherein said pushing tube assembly is composed of an inner tube and an outer tube, a hollow portion of said inner tube is used as a guiding wire channel and a sectional annular hollow portion between said inner tube and said outer tube is used as a leading wire channel.

3. A stent (or stent graft) locating device according to claim 1, wherein said pushing tube assembly is constructed of a single tube, a hollow portion of said single tube is used as a guiding wire channel and a plurality of leading wire channels are arranged in a wall of said tube at approximate regular intervals in a circumferential direction.

4. A stent (or stent graft) locating device according to claim 1, wherein said pushing tube assembly has a plurality of rigid leading wires which extend from an end of a leading wire channel and are scattered at approximate regular intervals in the circumferential direction.

5. A stent (or stent graft) locating device according to claim 1, wherein said pushing tube assembly has a plurality of rigid leading wires which extend from an end of a leading wire channel and are scattered at approximate regular intervals in the circumferential direction, and said plurality of rigid leading wires cross one another in a vicinity of end of said pushing tube assembly so as to form a course mesh.

6. A stent (or stent graft) locating device according to claim 4, wherein said pushing tube assembly has a plurality of rigid auxiliary leading wires which are finer and shorter than the rigid leading wires and extent among the number of rigid leading wires, from the end of said leading wire channel.

7. A stent (or stent graft) locating device according to claim 4, wherein said pushing tube assembly has a plurality of rigid lead-in wires which extend from the end of the leading wire channel and engaged with knees located at a terminal end of a stent at approximate regular intervals by detachable engaging means.

8. A stent (or stent graft) locating device according to claim 7, wherein said engaging means is a hook formed by bending the tip of each of said rigid lead-in wires.

9. A stent (or stent graft) locating device according to claim 7, wherein said engaging means is a ring screwed into the tip of each of said rigid lead-in wires.

10. A stent (or stent graft) locating device according to claim 1, wherein said rigid leading wires arc metallic wires of stainless steel, titanium nickel or nickel.

11. A stent (or stent graft) locating device according to claim 6, wherein said rigid auxiliary leading wires are metallic wires of stainless steel, titanium nickel or nickel.

12. A stent (or stent graft) locating device according to claim 7, wherein said rigid lead-in wires are metallic wires of stainless steel, titanium nickel or nickel.

13. A stent (or stent graft) locating device according to claim 1 in combination with a stent (or stent graft), wherein said stent (or stent graft) is encircled by the number of rigid leading wires and housed in said sheath.

14. A stent (or stent graft) locating device according to claim 13, wherein a tip of each of the number of rigid leading wires is seamed with an elastic ring-shaped portion of a stent (or stent graft) by a joining thread.

15. A stent (or stent graft) locating device according to claim 1, wherein each of the number of rigid leading wires has a length that is longer than each of the pushing tube assembly and the sheath.

16. A stent (or stent graft) locating device according to claim 1, wherein each of the number of rigid leading wires has a substantially uniform diameter that extends along a length of each of the leading wires to the free terminal end.

* * * * *